(12) United States Patent
Vellido et al.

(10) Patent No.: US 8,840,622 B1
(45) Date of Patent: Sep. 23, 2014

(54) IMPLANT INSTALLATION ASSEMBLY AND RELATED METHODS

(75) Inventors: Justin Vellido, San Diego, CA (US); Nathan Lovell, Oceanside, CA (US); Troy Woolley, Erie, CO (US)

(73) Assignee: NuVasive, Inc., San Diego, CA (US)

( * ) Notice: Subject to any disclaimer, the term of this patent is extended or adjusted under 35 U.S.C. 154(b) by 278 days.

(21) Appl. No.: 13/411,465

(22) Filed: Mar. 2, 2012

Related U.S. Application Data

(63) Continuation-in-part of application No. 12/378,685, filed on Feb. 17, 2009, now Pat. No. 8,343,163.

(60) Provisional application No. 61/448,594, filed on Mar. 2, 2011, provisional application No. 61/028,886, filed on Feb. 14, 2008, provisional application No. 61/105,384, filed on Oct. 14, 2008.

(51) Int. Cl.
| | |
|---|---|
| A61B 17/70 | (2006.01) |
| A61B 17/58 | (2006.01) |
| A61B 17/60 | (2006.01) |
| A61F 2/00 | (2006.01) |
| A61F 2/46 | (2006.01) |

(52) U.S. Cl.
CPC ............ *A61F 2/4611* (2013.01); *Y10S 606/914* (2013.01)
USPC ............................. 606/99; 606/86 A; 606/914

(58) Field of Classification Search
CPC ....................................................... A61F 2/4611
USPC ........................................... 606/86 A, 99, 914
See application file for complete search history.

(56) References Cited

U.S. PATENT DOCUMENTS

| | | | |
|---|---|---|---|
| 3,486,505 A | 12/1969 | Morrison | |
| 5,063,979 A | 11/1991 | Johnson | |
| 5,064,427 A * | 11/1991 | Burkinshaw | 606/99 |
| 5,320,625 A * | 6/1994 | Bertin | 606/91 |
| 5,431,658 A | 7/1995 | Moskovich | |
| 5,514,136 A * | 5/1996 | Richelsoph | 606/99 |
| 5,713,906 A * | 2/1998 | Grothues-Spork et al. | 606/99 |
| 5,860,973 A | 1/1999 | Michelson | |
| 6,159,215 A | 12/2000 | Urbahns | |
| 6,478,800 B1 * | 11/2002 | Fraser et al. | 606/99 |
| 6,652,533 B2 | 11/2003 | O'Neil | |
| 6,755,841 B2 | 6/2004 | Fraser | |
| 7,118,580 B1 | 10/2006 | Beyersdorff | |
| 7,169,182 B2 | 1/2007 | Errico | |
| 7,320,689 B2 | 1/2008 | Keller | |
| 7,404,795 B2 | 7/2008 | Ralph | |
| 7,722,622 B2 | 5/2010 | Evans | |
| 7,842,043 B2 * | 11/2010 | Errico et al. | 606/99 |
| 7,918,891 B1 | 4/2011 | Curran | |
| 8,142,441 B2 * | 3/2012 | Refai et al. | 606/99 |
| 8,343,163 B1 | 1/2013 | Arambula | |
| 8,343,164 B2 * | 1/2013 | Wallenstein et al. | 606/99 |
| 8,579,911 B2 * | 11/2013 | Dudasik | 606/99 |
| 2003/0028197 A1 * | 2/2003 | Hanson et al. | 606/99 |

(Continued)

*Primary Examiner* — David Bates
(74) *Attorney, Agent, or Firm* — Jonathan Spangler; Rory Schermerhorn

(57) ABSTRACT

This disclosure describes a guide assembly for guiding the installation of a spinal fusion implant to a surgical target site. The guide assembly includes a pair of arm members and a handle assembly that functions to clamp the arm members in locked and unlocked positions. The guide assembly interacts with an inserter to guide a spinal implant to the target site. Once the implant is inserted within the disc space, the guide assembly can be partially disassembled to facilitate removal from the surgical target site.

14 Claims, 14 Drawing Sheets

(56) References Cited

U.S. PATENT DOCUMENTS

| | | |
|---|---|---|
| 2004/0225295 A1 | 11/2004 | Zubok |
| 2005/0165408 A1 | 7/2005 | Puno |
| 2006/0241641 A1 | 10/2006 | Albans |
| 2007/0162040 A1 | 7/2007 | Grabowski |
| 2008/0114371 A1* | 5/2008 | Kluger ............................ 606/99 |
| 2008/0132902 A1 | 6/2008 | Bertagnoli |
| 2008/0154301 A1 | 6/2008 | de Villiers |
| 2008/0161817 A1 | 7/2008 | Parsons |
| 2009/0192611 A1* | 7/2009 | Lindner .................... 623/17.11 |
| 2009/0198339 A1 | 8/2009 | Kleiner |
| 2010/0234848 A1* | 9/2010 | Sutterlin et al. ................. 606/79 |
| 2012/0239097 A1* | 9/2012 | Garamszegi ................ 606/86 A |
| 2012/0277808 A1* | 11/2012 | May ........................... 606/86 A |
| 2013/0110184 A1* | 5/2013 | Wing et al. .................. 606/86 A |
| 2013/0282124 A1* | 10/2013 | Jodaitis et al. ............. 623/17.16 |

* cited by examiner

IMPLANT INSTALLATION ASSEMBLY AND RELATED METHODS

CROSS-REFERENCES TO RELATED APPLICATIONS

The present application claims the benefit of priority under 35 U.S.C. §119(e) from commonly owned and U.S. Provisional Application Ser. No. 61/448,594 filed on Mar. 2, 2011 and entitled "Implant Installation Assembly and Related Methods," and is a continuation-in-part of U.S. application Ser. No. 12/378,685 filed on Feb. 17, 2009 and entitled "Implant Installation Assembly and Related Method" which claims the benefit of priority under 35 U.S.C. §119(e) from commonly owned and U.S. Provisional Application Ser. No. 61/028,886 filed on Feb. 15, 2008 and entitled "Spinal Distraction and Implantation Assembly and Related Methods," and commonly owned and U.S. Provisional Application Ser. No. 61/105,384 filed on Oct. 14, 2008 and entitled "Spinal Distraction and Implantation Assembly and Related Methods," the entire contents of which are each hereby expressly incorporated by reference into this disclosure as if set forth fully herein. This disclosure also hereby incorporates by reference the entire contents of the following commonly-owned US Patents and commonly owned and co-pending US Patent Applications as if set forth fully herein: U.S. patent application Ser. No. 11/093,409, entitled "Systems and Methods for Spinal Fusion," filed on Mar. 29, 2005 and issued as U.S. Pat. No. 7,918,891 on Apr. 5, 2011; U.S. patent application Ser. No. 11/488,744, entitled "Spinal Fusion Implant and Related Methods," filed Jul. 17, 2006 and issued as U.S. Pat. No. 7,867,277 on Jan. 11, 2011; U.S. patent application Ser. No. 11/525,674, entitled "Spinal Fusion Implant and Related Methods," filed Sep. 22, 2006 and issued as U.S. Pat. No. 7,815,682 on Oct. 19, 2010; U.S. patent application Ser. No. 11/901,786, entitled "Systems and Methods for Spinal Fusion," filed on Sep. 18, 2007; U.S. patent application Ser. No. 12/329,195, entitled "Spinal Fusion Implant and Related Methods," filed Dec. 5, 2008; and U.S. patent application Ser. No. 12/396,458, entitled "Systems and Methods for Spinal Fusion and Deformity Correction," filed on Mar. 2, 2009.

FIELD

The present invention relates to delivering and implanting spinal implants during surgery.

BACKGROUND

The spine is formed by a column of vertebra that extends between the cranium and pelvis and includes three major regions known as the cervical, thoracic and lumbar regions. There are 7 cervical vertebrae, 12 thoracic vertebrae, and 5 lumbar vertebrae. These vertebrae are separated from one another by intervertebral discs that act as shock absorbers and allow the vertebrae to move relative to each other. A series of approximately 9 fused vertebrae extend from the lumbar region and make up the sacral and coccygeal regions of the vertebral column.

The main functions of the spine are to provide skeletal support and protect the spinal cord. If the normal physiology of the spine is disrupted due to trauma, degeneration, or other ailments, the delicate nervous tissue proximate the spine may be affected and the patient may experience symptoms ranging from discomfort to paralysis. In such instances surgical correction is often performed to relieve, or at least reduce, the patient's symptoms. Often times the surgical correction involves positioning an implant into the intervertebral space. This generally provides support and restores a more natural height to the disc space. The implants may be designed to provide a scaffold for bone ingrowth between the vertebra (i.e. fusion implant) or the implants may be designed to replace the function of the intervertebral disc (i.e. partial or total disc replacement).

SUMMARY

The present invention is directed at the separation of spinal vertebrae and the insertion of an implant within the vertebral space in a safe, accurate, and efficient manner. The installation device includes a first arm and a second arm immovably affixed to a handle and a pusher rod attached to a thumbwheel. The first and the second arm include a paddle at the distal end which are inserted while together or nearly together between the spinal vertebrae. Each paddle has grooves or ridges located on its outside surface which lie against the vertebral bone when inserted between the vertebrae to provide traction and prevent slippage. The width of each paddle increases vertically into a lip several millimeters from the end, which acts as a stopper for the insertion depth of the paddles into the intervertebral space. A notch in the center of each lip allows the vertebral edges to be visible when the paddles are inserted into the intervertebral space.

Between the first and second arm that result in the distal tip, there is a space to permit the insertion of an intervertebral implant into the device. The implant is placed between the arms and fastened to a pusher block. A parallel set of rails extend longitudinally along the upper and lower surface of the tail end of the pusher block and act to provide counter torque to the pusher block when the pusher rod is being moved forwards or back. The pusher block moves forward and back along the path of the arms. In one embodiment, the block has vertical side walls. In another embodiment, the block is solid, which increase the torsional strength of the parallel set of rails. The block is movable from a starting position adjacent to the handle forward to the distal tip end. The first and the second arms reside on the outside of the block as it is pushed forward and back. When an implant is inserted into the device and pushed towards the distal tip and paddles, the implant physically separates the paddles as they open to accommodate the width of the implant by slightly flexing the arms open. When the device is inserted into the spine and the paddles are located between the vertebrae, sliding the implant forward causes the paddles to spread the vertebrae apart and the vertebral space to widen to the height of the implant, creating an appropriate intervertebral space for insertion of the implant. In one embodiment, the inner surfaces of the non-parallel portion of the first and the second arms including the paddles are smooth to facilitate the implant sliding between them.

In one embodiment, the pusher block has guide elements on the distal end that move along each side of the top arm, assuring that the pusher block moves only axially directly forward or back along the first and the second arms. As the pusher block moves forward and back along the path of the first and the second arm it increases the surface area of the guide elements. During use, when the pusher block is extended distally, these guide elements rest against the vertebra, aiding in implant placement by preventing the implant from being pushed too far into the intervertebral space. When the pusher block is further advanced forward past the insertion point of the implant, this action causes the guide elements to press against the vertebra and forces the paddles and arms to be retracted from between the vertebrae, without disturbing the implant or requiring an additional tool for removal of the paddles. The removal force is transmitted to the vertebral body through the guide elements instead of to the implant itself, which might otherwise push the implant into an improper position. Additionally, the guide elements provide counter torque to the pusher block when the pusher rod is being moved forwards or back.

A section contains a thumbwheel for turning an internal threaded rod that extends through the pusher block and handle to attach and release the implant at the distal end of the device. The implant can be released by turning the thumbwheel until the internal threaded rod is twisted out of the implant attachment, such as when the implant is placed to remain within the intervertebral space. Other embodiments contemplate other attachment arrangements without departing from the scope of the present invention. The thumbwheel is equipped with ridged features along the radial surface to provide grips for the thumb, and the wheel is housed on two sides by an outer casing, preventing accidental turning of the wheel and facilitating turning the wheel with the thumb. At the end of the thumbwheel housing is a universal connector, which allows various handles or other devices (e.g. slap hammers, etc. . . . ) to be attached as desired by the user.

The device may be made from any number of suitable materials, including but not limited to titanium. Other embodiments contemplate other materials without departing from the scope of the present invention.

By way of example, in another embodiment, the first arm and the second arm may be elongated to better configure the spinal implant installation device for use through a surgical corridor formed via a lateral approach to the spine. According to this embodiment, the paddles may be detachably coupled to the first and second arms. By detachably coupling the paddles to the first and second arms, additional paddles of various sizes may be provided. The overall size, and particularly the length, of the distal end of the installation device may be adjusted according to the anatomical requirements of a particular patient or situation.

This may be particularly advantageous, for example, when the installation device is utilized to implant an intervertebral implant configured for lateral insertion due to the relatively large range of length dimensions associated with lateral implants. Closely matching the length of the paddles to the length of the selected implant will reduce the risk endplate damage resulting from excessive contact between anti-migration features on the surface of the implant and the endplate, while also ensuring that the paddles are not long enough to extend completely through the intervertebral disc space. According to one example, the paddles may be provided having lengths according to a range including, but not necessarily limited to, 40 mm-60 mm. In a preferred embodiment, paddles are provided in 40 mm, 50 mm, and 60 mm lengths. It will be appreciated that paddles may be provided according to any length suitable to traverse the particular intervertebral space.

Any of a number of configurations may be utilized to detachably couple the paddles to the first and second arms. According to the example embodiment pictured, a dovetail groove may extend through the distal end of arms from one side to the other. A complementary notch on the proximal end of each paddle may slide into groove. Though not shown, it will be appreciated that a stop may be provided on any of or any combination of the paddle, the notch, the arm, and the groove to prevent paddle from sliding all the way through groove. Arms may be further provided with aperture in open communication with the groove. Setscrews threadably advanceable through the apertures may engage the notches to lock paddles to the first and second arm during use.

BRIEF DESCRIPTION OF THE DRAWINGS

The invention will be more fully understood from the following detailed descriptions taken in conjunction with the accompanying drawings, in which.

DETAILED DESCRIPTION

Figure 1:
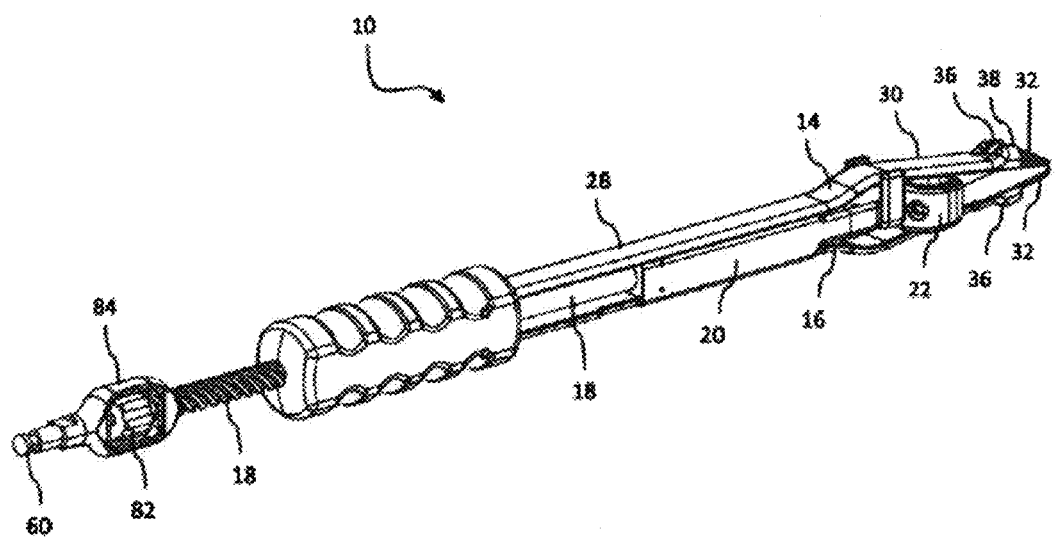
FIG. 1 is a perspective view of an implant installation device with an implant coupled thereto, according to one example embodiment.
Figure 2:
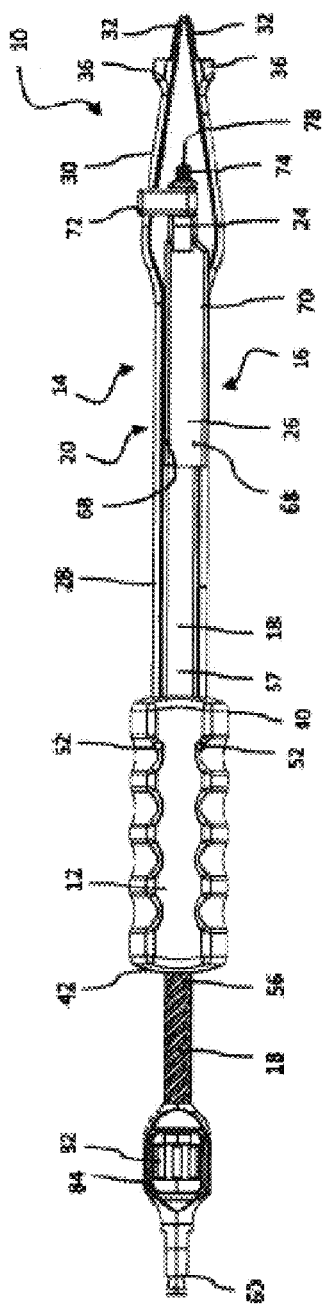
FIG. 2 is a side view of the implant installation device of FIG. 1, according to one example embodiment.
Figure 3:
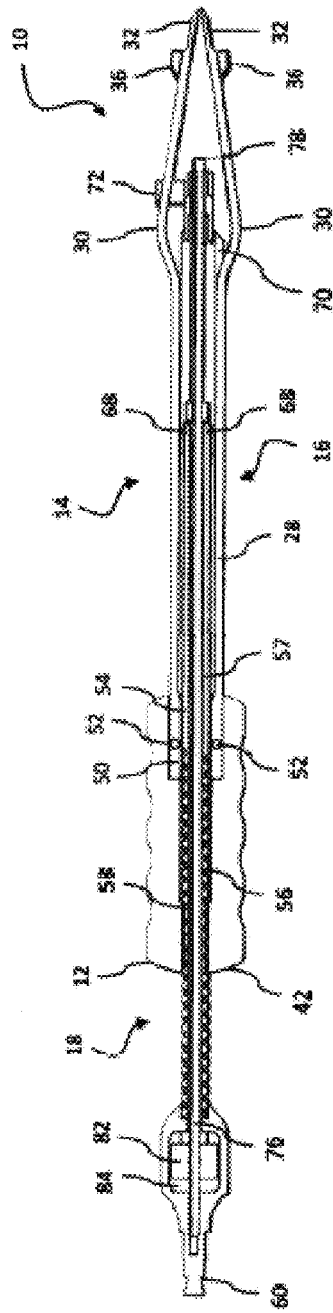
FIG. 3 is a cross-section of the side view of implant installation device as shown in FIG. 2, according to one example embodiment.
Figure 4:
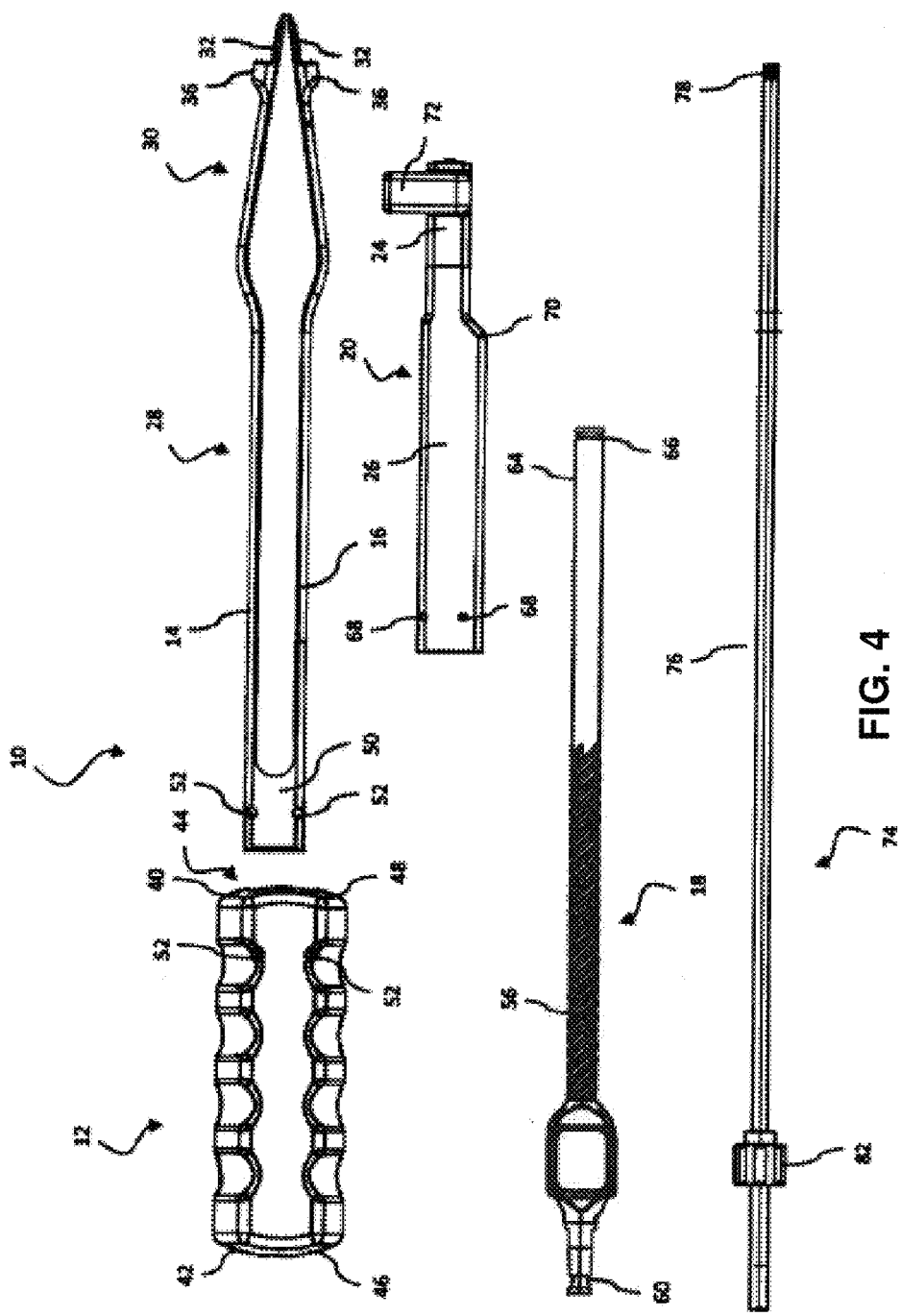
FIG. 4 is an exploded side view of the implant installation device of FIG. 1, according to one example embodiment.
Figure 5:
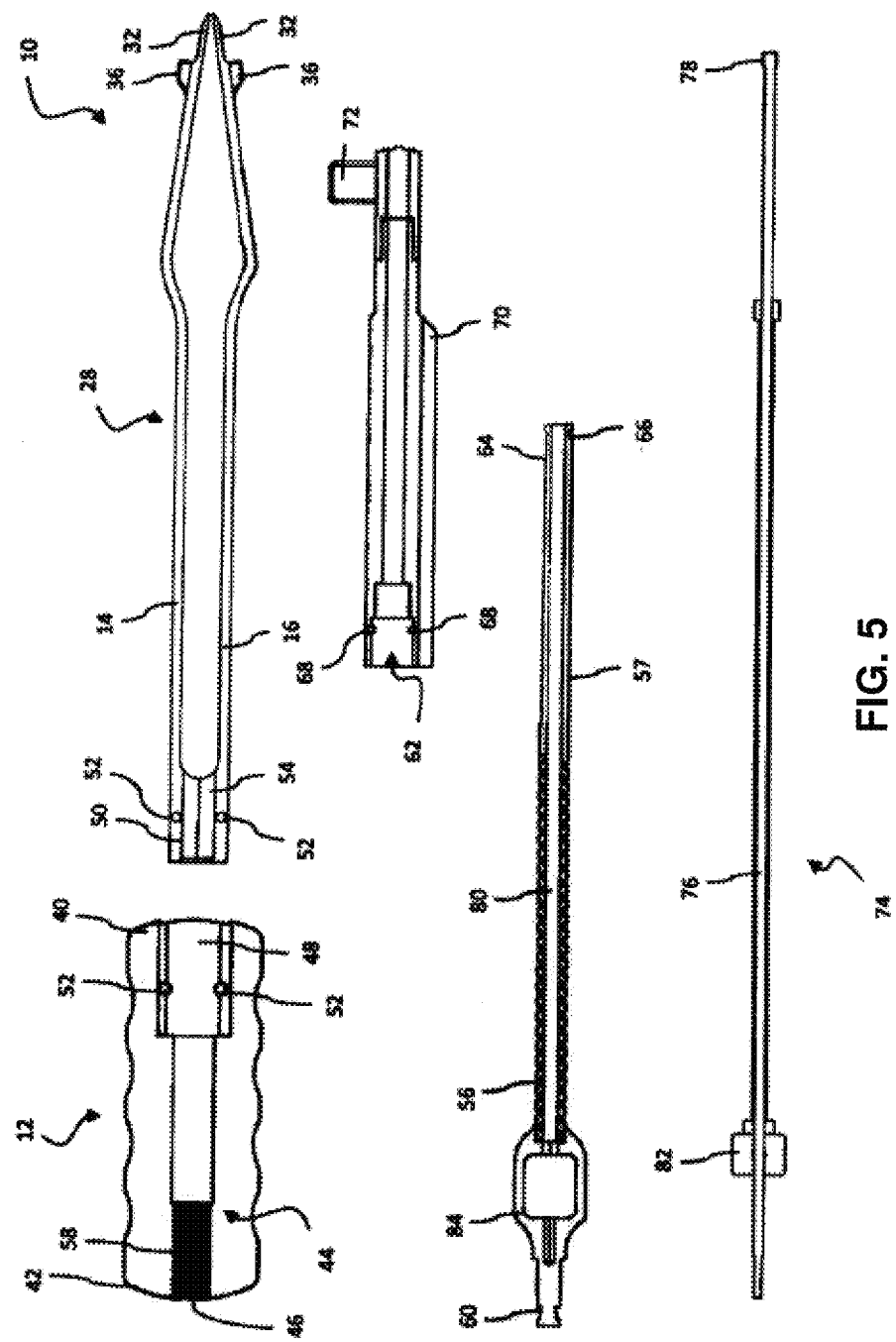
FIG. 5 is a cross-section of the exploded side view of implant installation device as shown in FIG. 4, according to one example embodiment.
Figure 6:
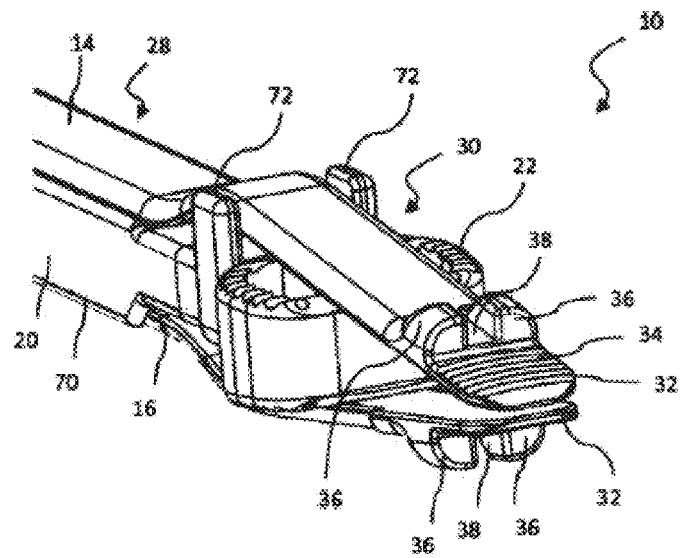
FIG. 6 is a perspective view of a distal end of the implant installation device of FIG. 1 with an implant coupled thereto, according to one example embodiment.
Figure 7:
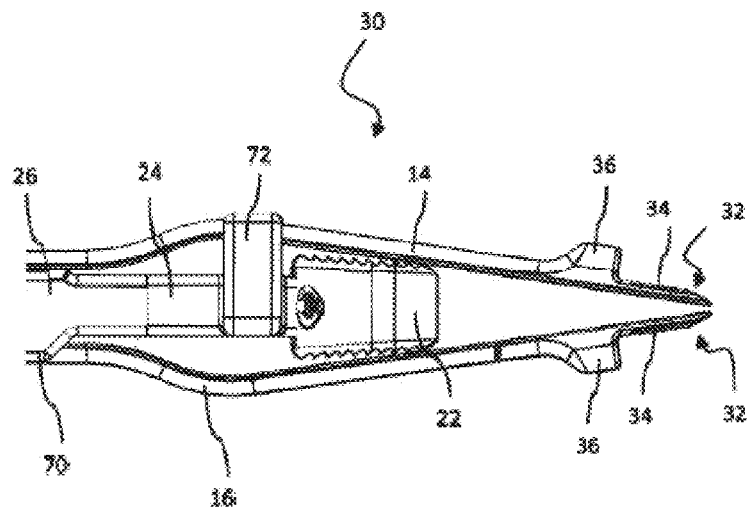
FIG. 7 is a side view of the distal end of the implant installation device as shown in FIG. 7, according to one example embodiment.

Illustrative embodiments of the invention are described below for the purposes of understanding the principles of the invention. No limitation of the scope of the invention is therefore intended. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The device disclosed herein boasts a variety of inventive features and components that warrant patent protection, both individually and in combination.

FIGS. 1-7 illustrate, according to one example embodiment, an implant installation device 10 for delivering an implant to a target site between a pair of vertebrae. The installation device 10 includes a handle 12 with a first arm 14 and a second arm 16 fixed to the handle 18 and extending distally therefrom. A translation member 18 is coupled to the handle 18 and extends through the handle such that a distal portion lies between the first arm 14 and second arm 16 while a proximal portion extends beyond the proximal end of the handle. An inserter 20 is coupled at the distal end of the translation member 18 and also lies between the first arm 14 and second arm 16. With an implant 22 positioned proximate the distal end of the inserter 20 the distal ends of the arms 14, 16 may be inserted between the pair of vertebrae. The translation member 18 may be operated to drive the inserter 20 distally, which in turn pushes the implant 22 forward (toward the disc space) between the arms 14, 16 until the implant enters the intervertebral disc space. By way of example only, the implant 22 may comprise one of the implants shown and described in the commonly owned and co-pending U.S. patent application Ser. No. 11/526,421, entitled, "Spinal Fusion Implant and Related Methods," filed on Sep. 25, 2006, the entire contents of which is expressly incorporated by reference as if set forth fully herein.

The interaction between the various components of the installation device may be best appreciated with reference to FIGS. 2-5. The first and second arms 16 may form a parallel region 28 proximate the handle 18, in which the first arm 14 and second arm 16 are generally parallel to one another, and a non-parallel region 30 proximate the distal end, in which the arms 14, 16 converge towards each other. The distal ends of arms 14, 16 form distraction tangs 32. Because the distraction tangs 32 converge at the distal end they may be easily advanced between the vertebrae without requiring prior distraction of the disc space. As the implant is advanced forward through the non-parallel region 30, the height of the implant will force the arms 14, 16 to flex apart such that the distraction tangs 32 (positioned between the vertebrae) will impart a separation force to the vertebrae and distract the disc space just enough to allow entry of the implant. As best viewed in FIG. 6, each distraction tang 32 may be provided with surface features 34 along the outer surface to enhance engagement with the vertebral endplates and prevent slippage or unwanted movement when the distraction tangs 32 are positioned in the disc space. By way of example only, the surface features 34 may include grooves, ridges, and/or teeth situated on at least a portion of the outer surface. Separating the distraction tangs 32 from the rest of the arms 14, 16 is an abutment 36 protruding vertically away from the respective arm 14 or 16. The abutment 36 acts as a stopper, limiting the depth to which the distraction tangs 32 may be inserted into the intervertebral space. This prevents the distraction tangs 32 from inadvertently being advanced beyond the opposing limits of the disc space, as well as to control the final positioning of the implant. A notch 38 in the center of each abutment 36 provides a sightline to the vertebral bodies when the distraction tangs 32 are inserted into the intervertebral space up to the abutment 36.

The handle 12 includes a distal end 40, a proximal end 42, and a central bore 44 extending the length of the handle 12. The central bore 44 includes first engagement region 46 for coupling with the translation member 18 and a second engagement region 48 for coupling to the first and second arms 14, 16. First and second arms 14, 16 may be connected to each other at a distal arm body 50 which is dimensioned to be snugly received within the second engagement region 48 of the handle 12. Pins (not shown) positioned in complementary pin holes 52 formed through the handle 12 and distal arm body 50 fix the arms to the handle. Distal arm body 50 includes a bore 54 in communication with the central bore 44 of the handle 12 at one end, and opening into a space between the first arm 14 and second arm 16 at the other end. The bore 54 is dimensioned to pass the translation member 18 there through such that the translation member 18 may extend from beyond the distal end 42 of the handle 12 through the bores 44 and 54 and into the space between the first arm 14 and second arm 16.

According to this example embodiment, at least a portion of the translation member 18 includes an exterior thread 56. A complementary interior thread 58 is situated in the first engagement region 46 of the handle 12 in order to movably couple the translation member 18 to the handle. Interior thread 58 and exterior thread 56 engage such that rotation of the translation member 18 causes the translation member 18 to move forward (distally) or backward (proximally) depending on the direction of rotation. In one embodiment, the exterior thread 56 stops proximally to distal portion 64 forming a non-threaded region 57. The non-threaded region may be provided of a length configured to stop backward movement of the inserter in a position where the implant 22, when attached, is located adjacent to the parallel region 28, at the proximal end of the non-parallel region 30. By starting the implant at this relatively forward position, the distance the implant must travel is minimal, reducing the time and effort required position the implant. A universal connector 60, such as, for example, a Hudson connector, may be provided at the proximal end of the translation member 18 to allow the attachment of accessories used to aid in imparting rotation to the translation member 18 (e.g. T-handles, gearshift handles, etc. . . . , not shown).

The inserter 20, including a forward body 24 and a trailing body 26, is situated in the space between the first arm 14 and the second arm 16. At the proximal end of the trailing body 26, the inserter 20 is rotationally coupled to the translation member 18. That is, the translation member 18 is longitudinally fixed to the trailing body 26 such that forward or backward movement of the translation member 18 will cause the inserter 20 to move in the same direction while permitting the translation member 18 to rotate freely relative to the inserter 20. To accomplish this, by way of example only, the trailing body 26 may include a bore 62 opening at the proximal end of the trailing body and dimensioned to receive a distal portion 64 of the translation member 18. The distal portion 64 of the translation member 18 may include a radial groove 66 situated therein. Pins (not shown) positioned through pin holes 68 engage the radial groove 66, denying longitudinal movement between the inserter 20 and translation member 18 while allowing for free rotation there between.

The trailing body 26 of the inserter 20 is dimensioned to slidably engage the inner surface of the first arm 14 and second arm 16 along the parallel region 28, having a height approximating the distance between the inner surfaces of the first arm 14 and second arm 16 in the parallel region 28. At least one pair of guide rails 70 extend vertically from the trailing body 26 capturing the sides of arm 16 there between. The guide rails 70 stabilize arm 16, providing a counter-torque when the translation member 18 is rotated to advance the inserter 20 and ensuring that the inserter 20 tracks forward smoothly and in-line with the arms 14, 16. The length of the trailing body 26 and the guide rails 70 that extend along the arm 16 is such that at least of portion of the parallel-region 28 is still situated between the guide rails 70 when the translation member 80 is advanced to the most distal position. If a single pair of guide rails 70 is utilized, as pictured in the embodiment of FIG. 1, the guide rails 70 should extend in a direction opposite the guide posts 72, described below, such that both arms 14 and 16 are captured by guide elements of the inserter 20.

The forward body 24 of the inserter 20 includes a pair of guide posts 72 that extend vertically on either side of the arm 14, capturing the sides of arm 14 there between. The guide posts 72 stabilize the arm 14, providing a counter-torque when the translation member 18 is rotated and again ensuring that the inserter 20 tracks forward smoothly and in-line with the arms 14, 16. The guide posts 72 are generally taller than the guide rails 70 because the guide posts engage the arm 14 in the non-parallel region 30 that is subject to greater height variation as the implant 22 is advanced towards the disc space. Additionally, the guide posts 72 are adapted to engage a face of one of the vertebra when the inserter 20 is fully advanced to deposit implant in the disc space. By engaging the vertebra, the guide posts 72 help facilitate the ejection of the distraction tangs 32 from the disc space without bothering the position of the implant. As the implant 22 enters the disc space and approaches the final desired position, the guide posts 72 engage the vertebra preventing any further advancement of the inserter 20. Further rotation of the translation member 18 thus causes the handle 12 to move proximally, pulling the distraction tangs 32 out of the disc space. In alternate embodiments, the guide posts 72 may be situated in various other arrangements. By way of example, an additional pair of guide posts may extend vertically in the opposite direction from the first guide posts such that guides posts capture both arms 14 and 16 there between. Alternatively, or in addition thereto, the guide posts 72 may be connected by a cross bar situated above and/or below one or both of arms 14, 16. The cross bar may further include a forward facing protrusion configured to engage the vertebral body instead of the guide post to effect removal of the distraction tangs 32.

Preferably, the implant 22 is temporarily attached in position in front of the inserter 20. An implant holder 74 may be included to hold the implant in place during insertion. As shown, by way of example, the implant holder comprises a rod 76 extending though a bore 80 in the translation member 18. The rod 76 is freely rotatable through the bore 80 and includes a threaded end 78 extending beyond the distal end of the forward body 24 and configured to engage a complementary threaded receiving aperture (not shown) on the implant 22. To temporarily fix the implant to the device 10 the implant is held in front of the threaded end 78 and the rod 76 is rotated until the threads of threaded end 78 mate with the threaded receiving aperture. To assist in rotating the rod 76, a thumbwheel 82 may be attached to a proximal portion of the rod 76. As shown, a thumbwheel housing 84 may be formed in the end of the translating member 18 to house the thumbwheel 82. While the implant holder has been described as utilizing a threaded connection to the implant 22, it will be appreciated that other attachment arrangements, such as for example, clamping or fork type arrangements may be used without departing from the scope of the present invention.

Figure 8:
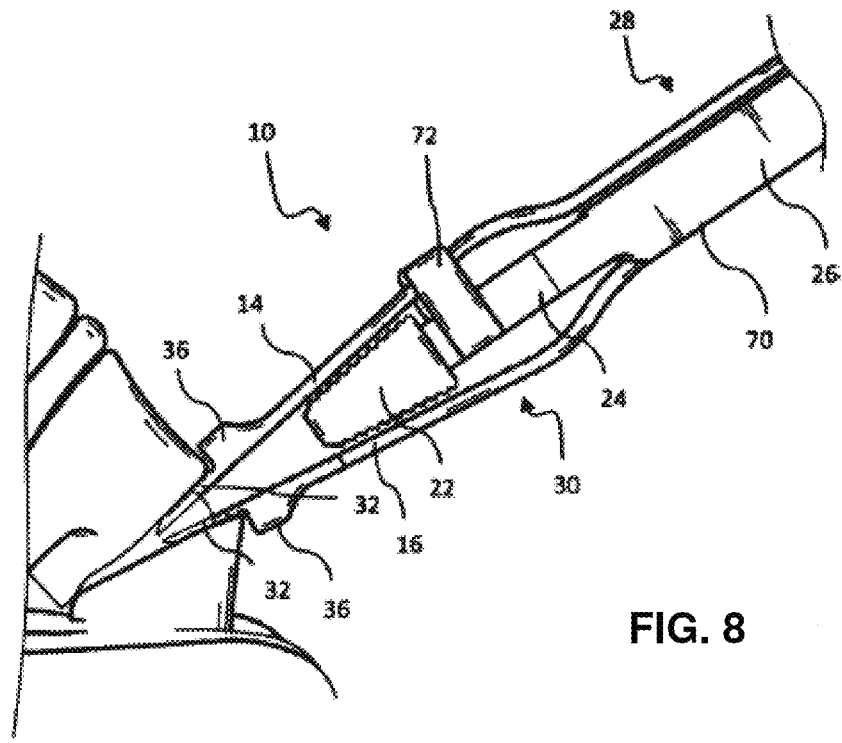
FIGS. 8-11 are side views illustrating steps performed during use of the implant installation device of FIG. 1, according to one example embodiment.
Figure 9:
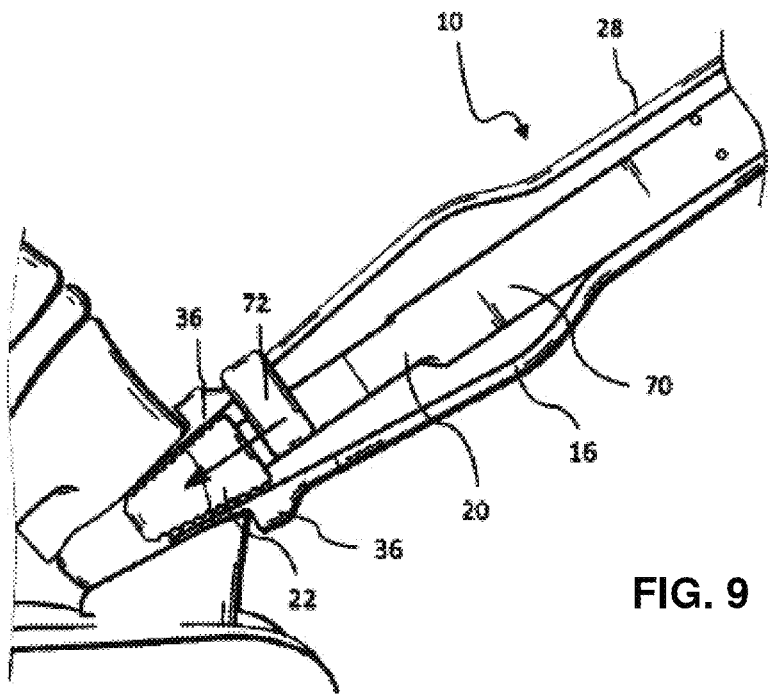
Figure 10:
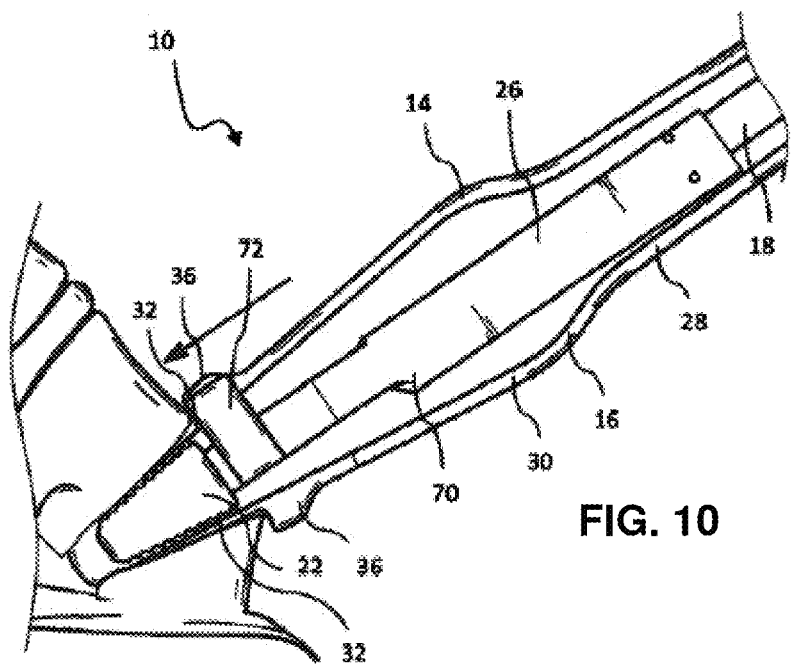

With reference to FIGS. 8-11, one surgical procedure utilizing the implant insertion device 10 to position an implant 22 between a pair of vertebrae will now be described. An access corridor is first created providing an avenue for delivering the insertion device 10 and the implant 22 attached thereto, to the intervertebral target site. By way of example only, FIGS. 8-10 illustrate the insertion device being used to deliver an implant through an anterior approach to the spine and the implant 22 is configured for such an approach. Once the access corridor is formed, the disc space may be prepared using conventional disc space preparation techniques and instruments, such as, for example, rasps, ronguers, curettes, etc. . . . The appropriate sized implant 22 may then be attached to the inserter 20 using the implant holder 74 and the installation device 10 may be passed through the operative corridor to the target spinal level. The distraction tangs 32 may then be inserted into the disc space between the vertebrae until the abutments 36 rest against the faces of the vertebral bodies, as depicted in FIG. 8. The surface features 34 on the distraction tangs will engage the vertebral end plates and help keep the distraction tangs 32 in the desired position. With the distraction tangs 32 positioned in the disc space and the abutments 36 resting on the vertebral bodies, the translation member 18 may by operated to advance the inserter 20 forward toward the disc space. When the translating member 18 is rotated, the exterior threads 56 advance along the interior threads 58 inside the handle 12 and thus moving the translating member 18 relative to the handle 12. As the translating member 18 moves forward toward the disc space the inserter 20 also moves forward driving the implant 22 though the non-parallel region 30 of the arms 14, 16. As, the implant 22 moves forward (FIG. 9) the height of the implant exerts a force on the arms 14, 16 causing them to flex away from each other. The distraction force is delivered to the vertebral bodies via the distraction tangs 32 and the disc space is distracted to a height determined by the height of the implant 22. The distraction tangs 32 also act as a guard to the vertebral endplates, preventing gouging or other damage that could occur if the implant 22 was forced into the disc space in direct contact with endplates.

Figure 11:
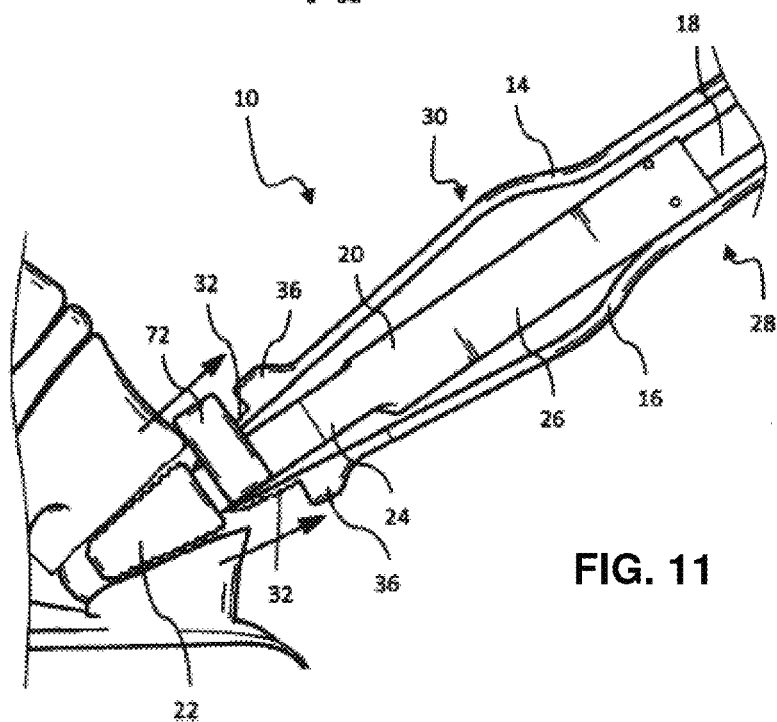

As the implant 22 is fully received within the disc space, the guide posts 72 come into contact with the upper vertebral body, as shown in FIG. 10. With the guide posts 72 in contact with the vertebral body, additional advancement of the translating member 18 causes the handle 12 and arms 14, 16 to move backward relative to the inserter 20 withdrawing the distraction tangs 32 from the disc space, as illustrated in FIG. 11. Once the distraction tangs 32 are free from the disc space, the implant holder 74 may be released from the implant 22 and the implant installation device may be removed from the operative corridor, which may be subsequently closed.

While the example embodiment of the implant installation device 10 was shown above in use through an anterior approach, it will be appreciated that the device may be utilized to access the spine using other approaches (e.g. anterolateral, lateral, posterolateral, and posterior approaches). Also the implant may utilized to access the spine in any of the different spinal regions. To accommodate the different anatomies (e.g. size, etc. . . . ) found in the different spinal regions, the dimensions of the device may be adjusted accordingly, for the device as a whole or for any individual or combination of individual components and/or features. Similarly, the dimensions of the device may adjusted for the device as a whole or for any individual or combination of individual components and/or features, as appropriate for the desired approach. It will also be appreciated that the implant to be delivered, including the size and footprint may vary according to the spinal region and desired approach.

Figure 12:
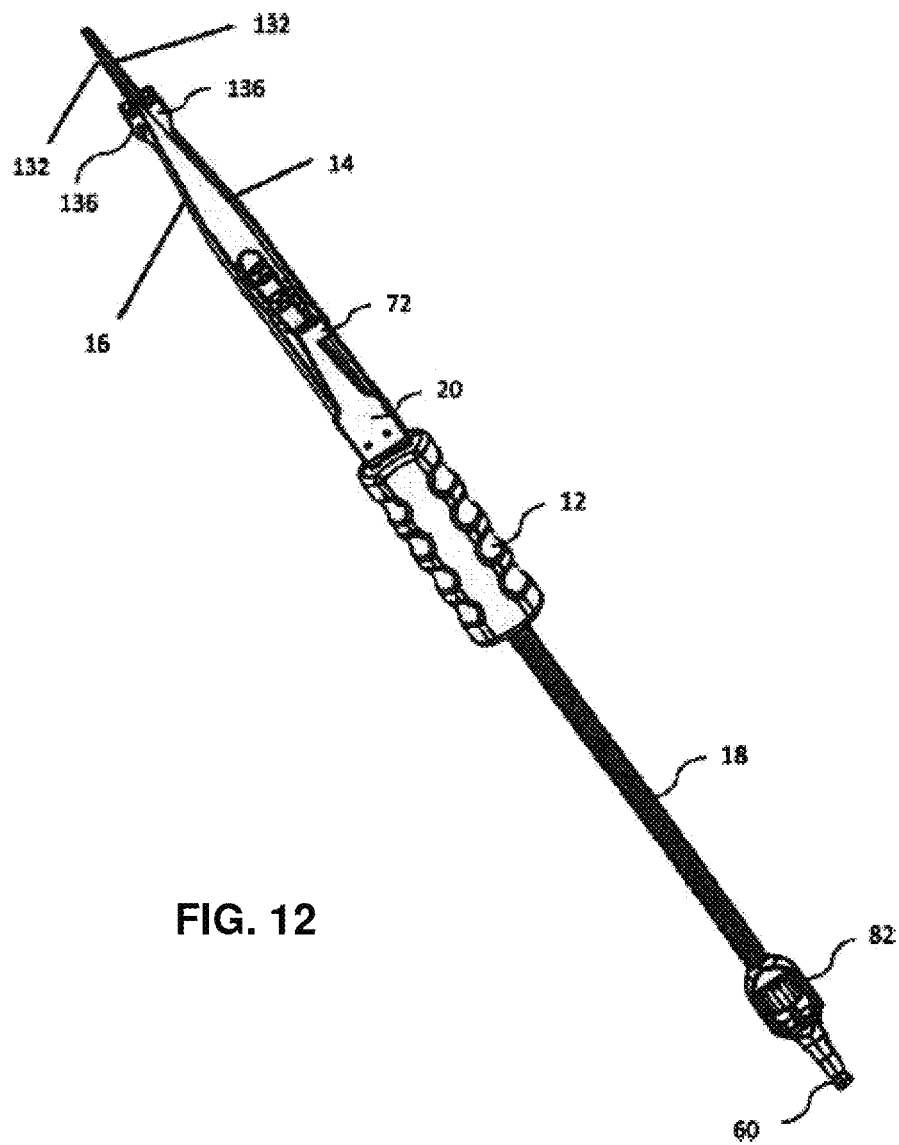
FIG. 12 is a is a perspective view of an implant installation device with an implant coupled thereto, according to another example embodiment.
Figure 13:
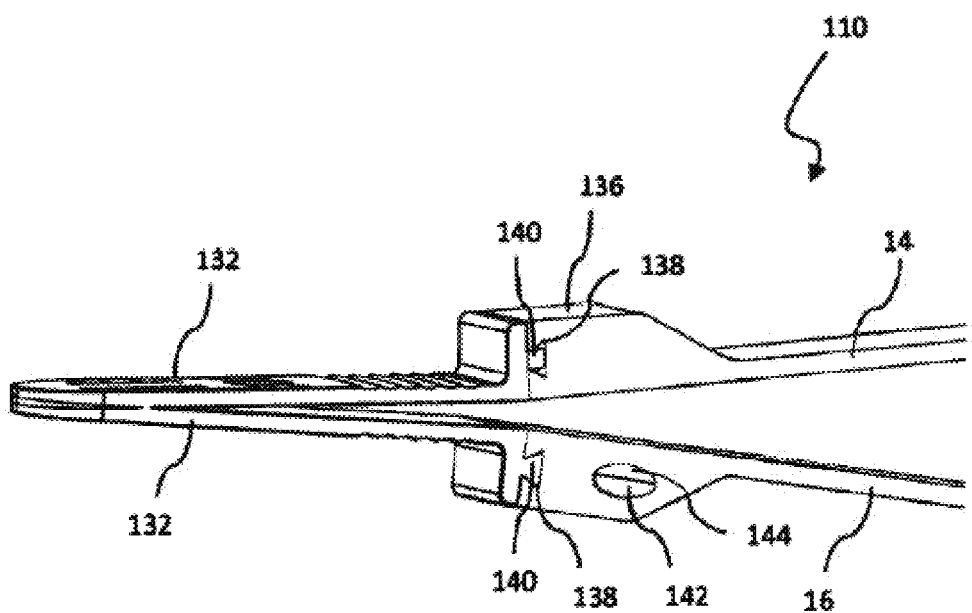
FIG. 13 is a side view of the distal end of the implant installation device of FIG. 12, according to one example embodiment.

By way of example, another example embodiment is shown in FIGS. 12 and 13. The implant installation device 110, shown in FIGS. 12 and 13 shares many common elements with the installation device 10 such that repeat discussion of the common elements is unnecessary. For simplicity, identical callouts have been used to common elements. The dimensions of installation device 110 have been slightly modified as compared to the installation device 10 to better configure the implant installation device 110 for use through a surgical corridor formed via a lateral approach to the spine. According to this embodiment, distraction tangs 132 may be detachably coupled to the first and second arms 14, 16. By detachably coupling the distraction tangs 132 to the first and second arms 14, 16, distraction tangs 132 of various sizes may be utilized based on the particular anatomy of the patient. This may be particularly advantageous, for example, when the installation device 10 is utilized to deliver an implant 122 configured for lateral insertion, such as the implants shown and described, by way of example only, in the commonly owned and co-pending U.S. patent application Ser. No. 11/093,409, entitled "Systems and Methods for Spinal Fusion," filed on Mar. 29, 2005 and issued as U.S. Pat. No. 7,918,891 on Apr. 5, 2011; U.S. patent application Ser. No. 11/901,786, entitled "Systems and Methods for Spinal Fusion," filed on Sep. 18, 2007; and U.S. patent application Ser. No. 12/396,458, entitled "Systems and Methods for Spinal Fusion and Deformity Correction," filed on Mar. 2, 2009, the entire contents of each being incorporated herein by reference as if set forth fully herein. As previously mentioned, the distraction tangs 132 act as a guard when they are situated between the implant and the vertebral endplate. Closely matching the length of the distraction tangs 132 to the length of the selected implant may reduce the risk of endplate damage during implant delivery, while also ensuring that the distraction tangs 132 are not long enough to extend completely through the intervertebral disc space. It will be appreciated that distraction tangs 132 may be provided according to any range of lengths suitable to traverse a particular intervertebral space. According to one example, the distraction tangs 132 may be provided having lengths within a range including, but not necessarily limited to, 40 mm-60 mm. According to one example, a pair of distraction tans 132 may be provided for each of the lengths 40 mm, 50 mm, and 60 mm.

Any of a number of configurations may be utilized to detachably couple the distraction tangs 132 to the first and second arms 14, 16. As shown in the pictured embodiment, by way of example only, abutments 136 may include a grooves 138 extending laterally across the face of the abutments. As shown, the grooves 138 are a dovetail grooves. A complementary notch or ridge 140 situated on the proximal end of each distraction tang 132 may be slidably received within the grooves 138. Though not shown, it will be appreciated that a stop(s) may be provided on any of or any combination of the distraction tang 132 and the notch 140 to prevent the distraction tangs 132 from sliding all the way through grooves 138. According to one example, to temporarily fix the distraction tangs 132 to the arms 14, 16, the abutments 136 may be further provided with apertures 142 in open communication with the grooves 138. Setscrews 144 may be advanced through the apertures 142 such that they may engage the notches 140, locking the distraction tangs 132 in position.

It will also be appreciated that the non-parallel region 30 of the arms 14, 16 is longer than that of the device 110 to better accommodate the lateral approach. Rather than extending outward first and then converging together sharply to create space for the implant in the relatively short non-parallel region 30 of the installation device 10, the non-parallel region 30 of installation device 110 is extended and the arms 14, 16 converge towards each other directly. This creates a sleeker profile and allows the installation device to be advanced through smaller corridors (such as for example, retraction and/or distraction assemblies used to access the lateral aspect of the spine).

FIGS. 14-22 illustrate an example of a guide assembly 210 according to another embodiment of the invention. The guide assembly 210 according to this embodiment is particularly suited to delivery of implants through a posterior approach (e.g. PLIF, TLIF approaches), however, use through other approaches is possible without departing from the scope of the invention. The guide assembly 210 is designed to work in conjunction with an independent implant inserter 300 having an elongated cylindrical shaft for facilitating the insertion of an implant 310 into a surgical target site. The guide assembly 210 helps guide the implant into position, without damage to endplates from the impaction method of insertion.

Figure 16:
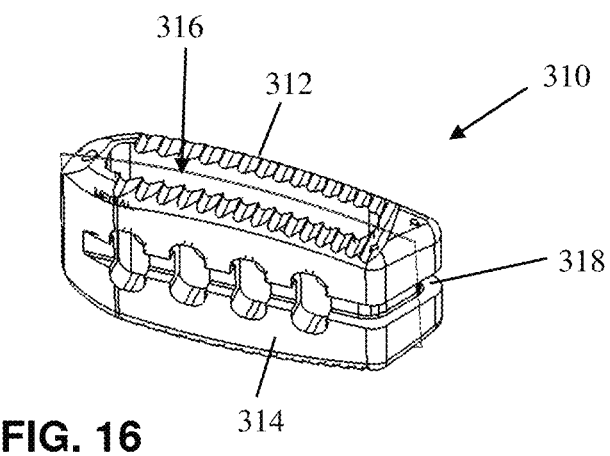
FIG. 16 is a perspective view of one example of an implant suitable for use with the guide assembly of FIG. 14.
Figure 17:
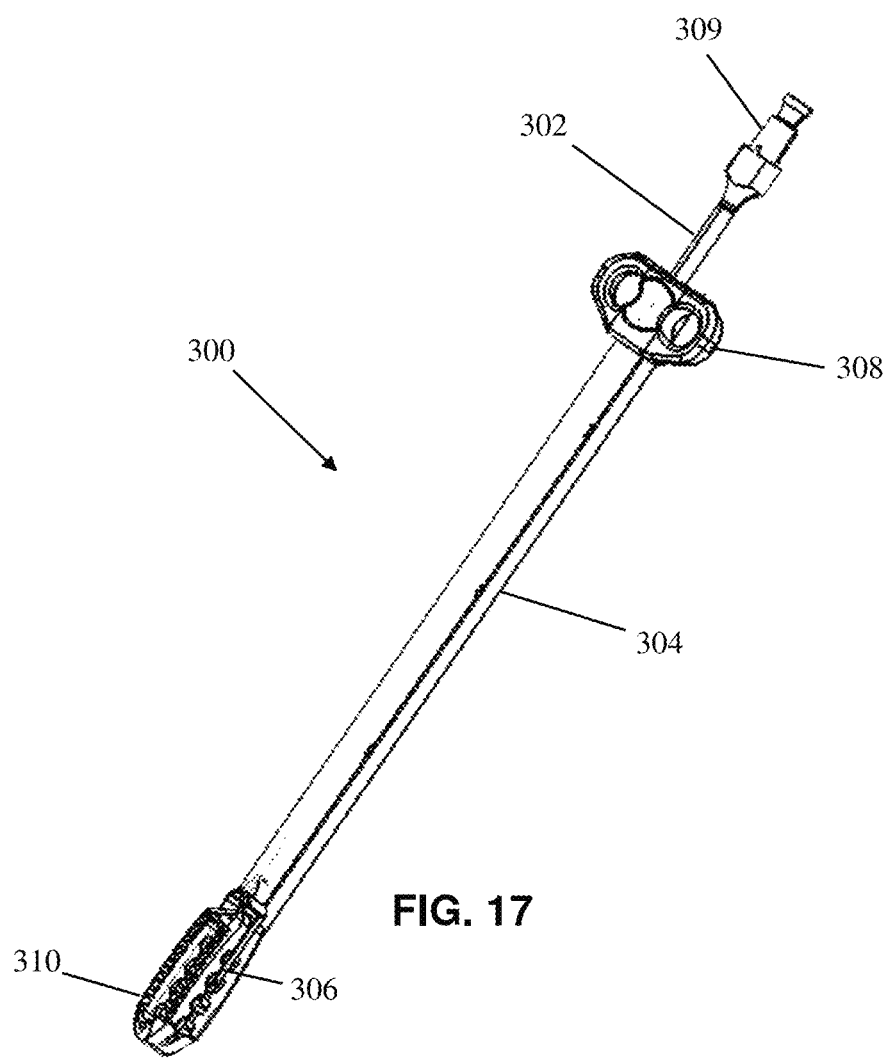
FIG. 17 is a perspective view of the implant of FIG. 16 coupled to the implant inserter of FIG. 14.

Referring first to FIGS. 16 and 17, examples of a spinal implant 310 (FIG. 16) and implant inserter 300 (FIG. 17) suitable for use with the guide assembly 210 are provide in order to better illustrate the structure and function of the guide assembly 210. The spinal implant 310 shown by way of example only is one that is configured for use during a transforaminal lumbar interbody fusion (TLIF) procedure and is of the type shown and described in the above-referenced commonly owned U.S. Pat. No. 7,918,891, the contents of which are hereby incorporated by reference into this disclosure as if set forth fully herein. The guide assembly 210 is capable of being used with other implant/inserter combinations, such as (by way of example) the implants and inserters shown and described in the above-referenced U.S. Pat. Nos. 7,867,277 and 7,815,682 and the above-referenced U.S. patent application Ser. No. 12/329,195, the contents of which are hereby incorporated by reference into this disclosure as if set forth fully herein. The spinal implant 310 is generally rectangular in shape and has four longitudinal side surfaces including an opposing pair of vertebra-engaging surfaces 312 and an opposing pair of smooth side surfaces 314. The spinal implant 310 further includes a fusion aperture 316 and an engagement groove 318 extending substantially around the periphery of the spinal implant 310 for engaging with the inserter 300. The fusion aperture 316 may be configured to receive fusion-promoting material for use to help enhance the bone fusion process.

The implant inserter 300 includes an inner shaft 302 and an outer sleeve 304. The inner shaft 302 includes a pair of prongs 306 at the distal end of the inner shaft 302, the prongs 306 being configured to engage the engagement groove 318 of the spinal implant 310. The outer sleeve 304 includes a rotating knob 308 which, when rotated, advances the outer sleeve 304 over a tapered base potion of the prongs which squeezes the prongs together and locks the implant 310 and inserter 300 together. The proximal end of the inner shaft 302 includes a connector 309 (for example a Hudson-type connector) for connecting one or more auxiliary attachments (not shown, but for example a T-handle, slap hammer, and the like) to use with the implant inserter 300.

Figure 14:
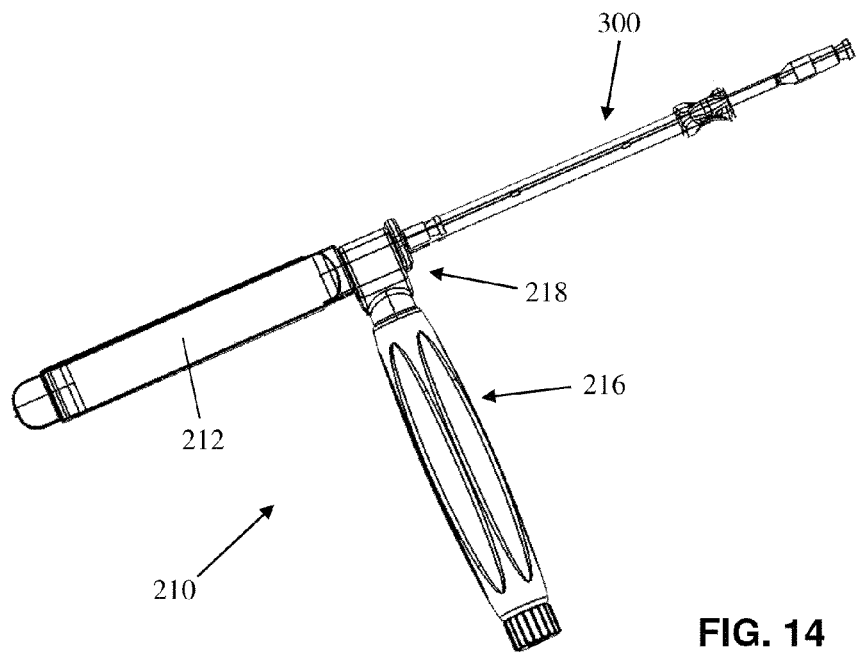
FIG. 14 is a side view of an example of a guide assembly according to another embodiment of the present invention coupled with an implant inserter.
Figure 15:
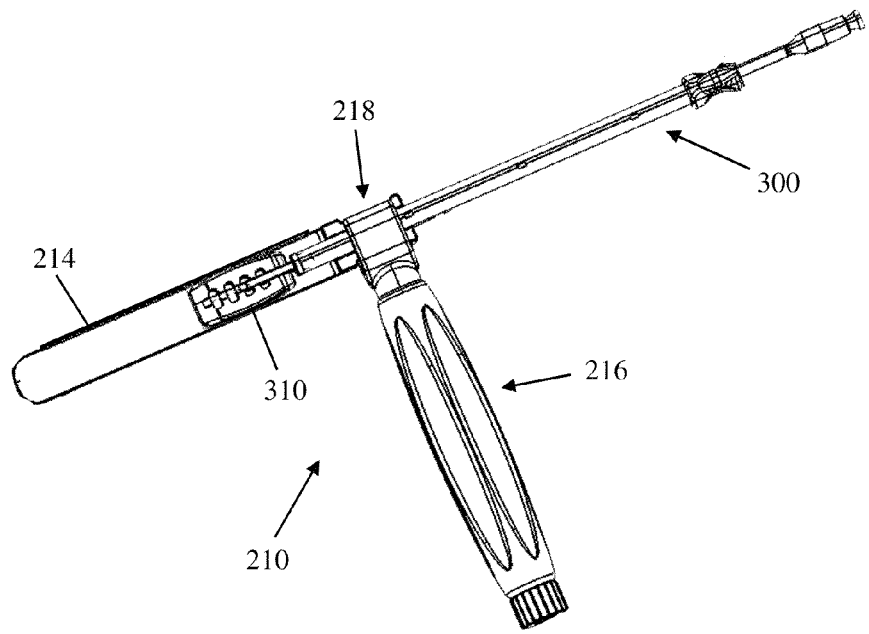
FIG. 15 is a side view of the guide assembly coupled with the implant inserter of FIG. 14, with one of the arm members forming part of the guide assembly removed to show the positioning of the implant and inserter relative to the guide assembly upon initial coupling of the implant, implant inserter, and guide assembly.

Referring now to FIGS. 14 and 15, the guide assembly 210 includes a first arm member 212, a second arm member 214 and a handle assembly 216. The first and second arm members 212, 214 cooperate to form a distraction corridor for the spinal implant 310 to pass through. The first and second arm members 212, 214 are held in place together by the handle assembly 216 at the attachment region 218. As will be explained in greater detail below, when the guide assembly 210 is fully assembled and coupled with an implant inserter 300 (with attached implant 310), the first and second arm members 212, 214 are coupled together by the handle assembly 216, with the implant inserter 300 extending longitudinally therethrough and the implant 310 positioned between the arm members 212, 214. In this fashion, once the guide assembly has been properly positioned within the surgical target site, the implant 310 can be distally advanced along the arm members 212, 214 and inserted into the target disc space.

Figure 18:
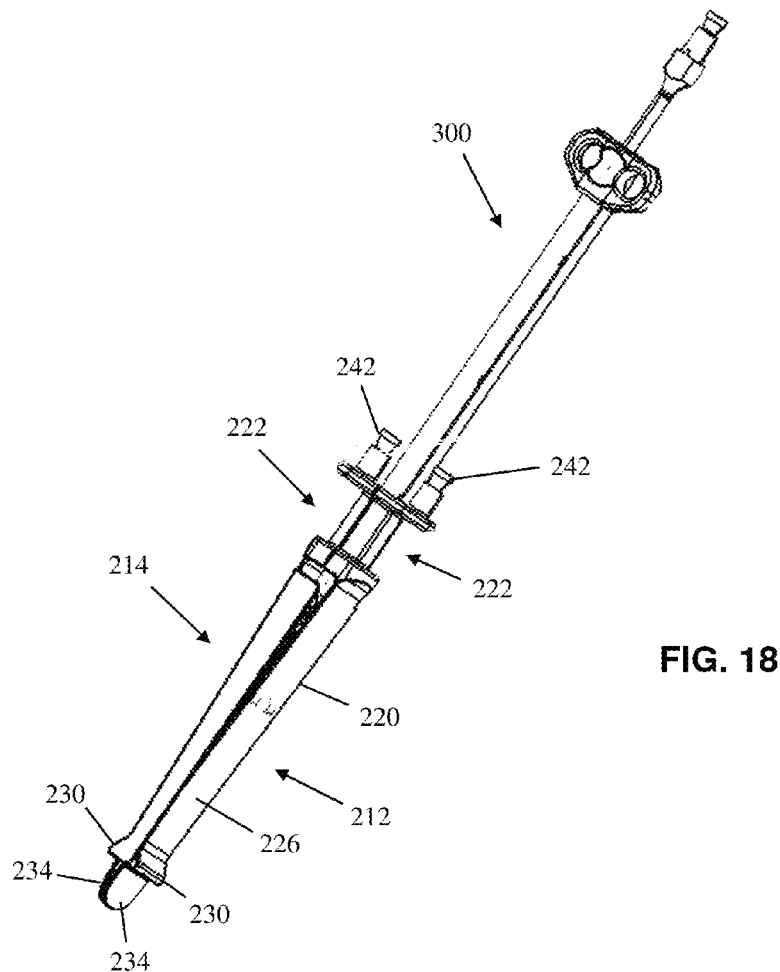
FIG. 18 is a perspective view of the guide assembly coupled with the implant inserter of FIG. 14 with the handle assembly removed.
Figure 19:
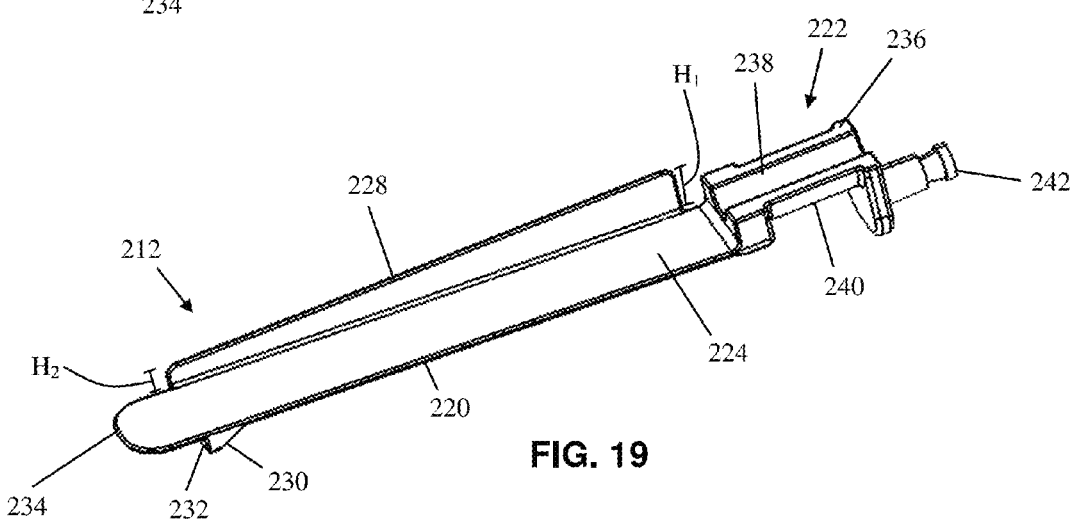
FIG. 19 is a perspective view of an arm member forming part of the guide assembly of FIG. 14.
Figure 20:
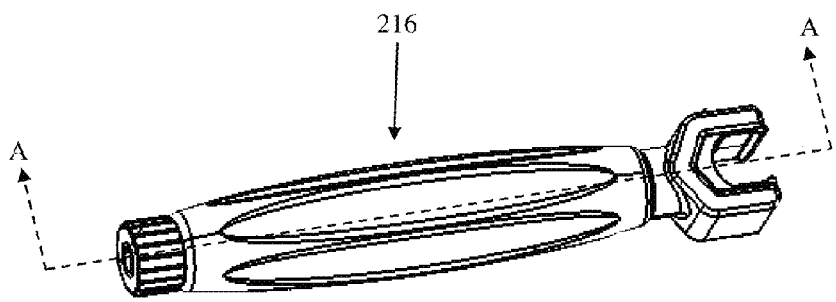
FIG. 20 is a perspective view of a handle assembly forming part of the guide assembly of FIG. 14.
Figure 21:
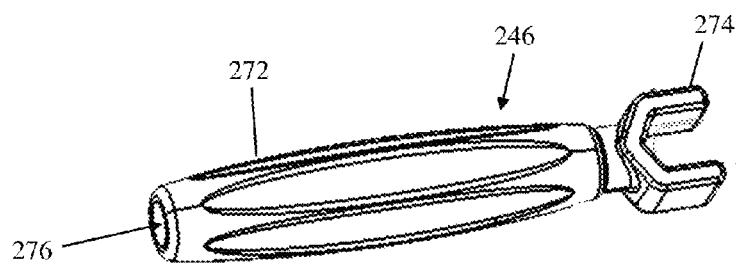
FIG. 21 is a perspective view of an outer sleeve forming part of the handle assembly of FIG. 20.
Figure 22:
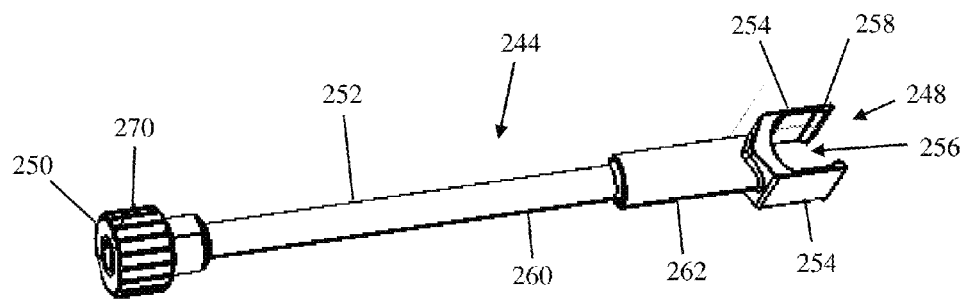
FIG. 22 is a perspective view of an inner sleeve forming part of the handle assembly of FIG. 21.
Figure 23:
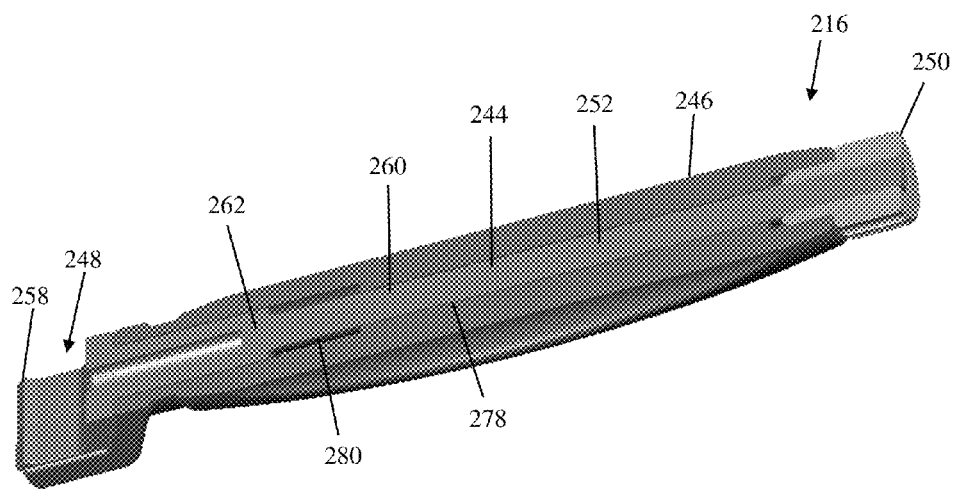
FIG. 23 is a perspective view of a cross section of the handle assembly of FIG. 20, taken along line A-A in FIG. 20.
Figure 24:
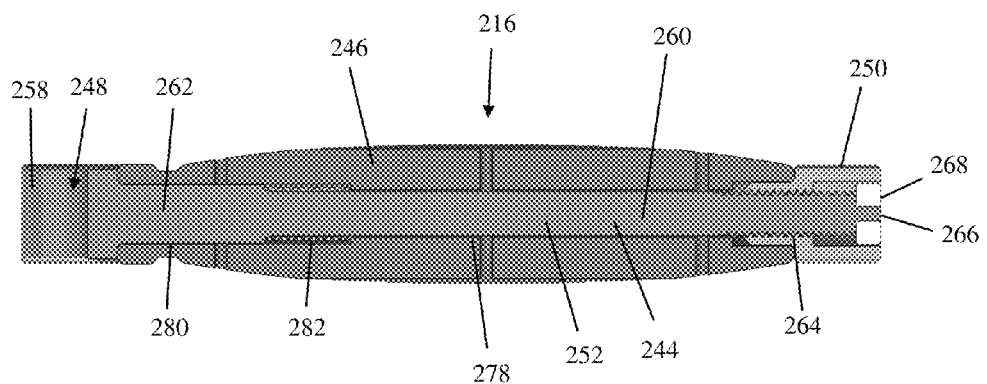
FIG. 24 is a side view of the cross section of the handle assembly of FIG. 23.

FIGS. 18 and 19 illustrate the first and second arm members 212, 214 in greater detail. The first and second arm members 212, 214 are substantially identical in form and thus description of the various details will be limited to the first arm member 212. However, it should be understood that for each feature described in relation to the first arm member 212, the second arm member 214 has an identical and complementary feature. The first arm member 212 has an elongated guide member 220 extending distally from an attachment region 222. By way of example only, the guide member 220 is generally rectangular in shape and has an inner surface 224 and an outer surface 226. By way of example, the inner and outer surfaces 224, 226 are generally planar, however other configurations are possible. The generally planar configuration of the inner and outer surfaces 224, 226 function to provide a smooth plane for guiding the implant 310 into the target disc space and also to help keep fusion-promoting material (if any) from escaping the fusion aperture 316 during insertion. The guide member 220 further includes a side rail 228 extending longitudinally along one side of the guide member 220 and protruding generally perpendicularly from the guide member 220. By way of example, the side rail 228 has a proximal height dimension $H_1$ and a distal height dimension $H_2$ and is generally tapered in shape such that $H_1 > H_2$. When the guide assembly 210 is fully assembled, the guide members 220 and side rails 228 function to provide a substantially enclosed corridor for advancing the spinal implant 310 to the target disc space. The side rails 228 also provide additional stability by limiting lateral flex during distraction, and provide extra insurance that the spinal implant 310 follows the intended trajectory during insertion. The guide member 220 further includes an abutment 230 positioned on the outer surface 226. The abutment 230 has a distally-facing abutment surface 232 configured to engage a vertebral endplate during use. The guide member 220 further includes a distraction tang 234 extending distally from the abutment 230. The distraction tang 234 is configured such that it has an inner surface that is continuous with the inner surface 224 of the guide member 220.

The attachment region 222 extends proximally from the proximal end of the guide member 220. The attachment region 222 has a generally planar inner surface 236 and a semi-cylindrical channel 238 having a concave curvature extending longitudinally therethrough. When the guide assembly 210 is fully assembled, the attachment regions 222 are mated at the generally planar inner surfaces 236 and the semi-cylindrical channels 238 cooperate to form a single cylindrical channel for receiving the implant inserter 300. The attachment region 222 further includes an outer semi-cylindrical surface 240 having a convex curvature extending semi-circumferentially around the attachment region 222. When the guide assembly 210 is fully assembled, the outer semi-cylindrical surfaces 240 cooperate to form a single attachment surface that extends circumferentially around the first and second arm members 214, 216 to facilitate attachment of the handle assembly 216, as will be described in further detail below. The proximal end of the attachment region 222 has a connector 242 (for example a Hudson-type connector) for connecting one or more auxiliary attachments (not shown, but for example a T-handle, slap hammer, and the like) to use with the guide member 220.

Referring now to FIGS. 20-24, the handle assembly 216 includes an inner member 244 and an outer sleeve 246. The inner member 244 includes a clamp 248 located at a distal end, a locking knob 250 located at a proximal end, and an elongated shaft 252 extending therebetween. The clamp 248 includes a pair of clamp arms 254 extending in a distal direction and collectively forming a generally U-shaped receiving area 256. The distal end of each of the clamp arms 254 includes a tapered lip 258 on an inward-facing surface (i.e. within the receiving area 256). The tapered lip 258 has a bi-directional taper to allow for both attachment and release of the first and second arm members 214, 216, as will be describe below. The receiving area 256 is dimensioned to interface with the outer semi-cylindrical surface 240 of the attachment region 222 of each of the first and second arm members 212, 214. The elongated shaft 252 is generally cylindrical and by way of example may be provided two sections having different diameters. For example, shaft 252 includes a first section 260 that extends from the proximal end toward the distal end. Near the distal end, the shaft 252 has a second section 262 having a diameter that is greater than the diameter of the first section. The proximal end of the shaft 252 has a threaded region 264 to engage the locking knob 250 and a post 266 with an attached plug 268 that prevents the locking knob 250 from disengaging the shaft 252. The locking knob 250 has a contoured outer surface 270 to provide traction for a user. In the example provided, the contoured outer surface comprises grooves, however other traction providing elements are possible. The locking knob 250 further has an interior channel having threads to threadedly engage the proximal end of the elongated shaft 252.

The outer sleeve 246 includes an elongated handle body 272 having a contoured outer surface to provide traction to a user, a clamp frame 274 located at the distal end and dimensioned to receive the clamp 248 of the inner member 244, and a channel 276 extending longitudinally through the outer sleeve 246. The clamp frame 274 is rigid and provides protection and solidity for the otherwise flexible clamp 248 during use. The channel 276 is dimensioned to receive the elongated shaft 252 of the inner member 244, and thus has a first section 278 with a diameter complimentary to the diameter of the first shaft section 260, and a second section 280 with a diameter complimentary to the diameter of the second shaft section 262. A spring 282 is positioned within the second section 280 such that it interacts with the second shaft section 262 to bias the shaft in a distal (forward) direction. This biasing keeps the locking knob 250 in position at the end of the outer sleeve 246 when the locking knob 250 is loosened and the handle assembly 216 is in an "unlocked" state.

Assembly and use of the guide assembly 210 will now be described in conjunction with an example implant inserter 300 and spinal implant 310 as described herein above. However, use of the guide assembly 210 is not limited to the specific example shown and described herein as use with other spinal implants and implant inserters is possible. Prior to engaging the guide inserter 210, a spinal implant 310 is coupled to an implant inserter 300. To use the guide assembly, the first and second arm members 214, 216 are placed on opposite sides of the implant inserter 300 such that the outer sleeve 304 of the implant inserter 300 is positioned longitudinally within the channel 238 of the first and second arm members 214, 216, and the inner surfaces 236 of the first and second arm members 214, 216 are mated against one another. When positioned properly, the spinal implant 310 is located between the guide members 220 of the arm members 214, 216. Next the handle assembly 216 is set to the "unlocked" position by turning the locking knob 250 in the unlock direction (e.g. counter clockwise). This translates the inner shaft 252 in a distal (forward) direction based on the threaded connection to the locking knob 250 and the spring 282 that keeps the locking knob 250 forced against the outer sleeve 246. In the unlocked position the clamp arms 254 extend distally beyond the clamp frame 274. The handle assembly 216 is then mated with the arm members 214, 216 by placing the outer semi-cylindrical surfaces 240 of the first and second arm members 214, 216 within the receiving area 256 of the clamp 248. During this mating process, the clamp arms 254 will flex slightly outward as the tapered lips 258 pass over the outer surfaces 240 of the first and second arm members 214, 216. When the outer surfaces 240 of the first and second arm members 214, 216 are properly positioned within the receiving are 256, the clamp arms 254 return to their initial position and the tapered lips 248 prevent the first and second arm members 214, 216 from becoming easily dislodged. The handle assembly 216 is then "locked" by turning the locking knob 250 in a clockwise direction. This causes the inner shaft 252 to translate in a proximal direction, which pulls the clamp arms 254 into/against the clamp frame 274. The rigid clamp frame 274 prevents the clamp arms 254 from flexing outward, and thus because of the tapered lips 248 the first and second arm members 214, 216 are prevented from becoming dislodged from the handle assembly 216. The handle assembly 216 is now in a "locked" configuration and the guide assembly 210 is securely attached to the implant inserter 300.

The guide assembly 210 is then used to advance the implant inserter 300 with the attached spinal implant 310 through a surgical access corridor to a target disc space. The distraction tangs 234 enter the disc space and the abutment surfaces 232 of the abutments 230 rest against the adjacent vertebral bodies to prevent over insertion of the distraction tangs 234. The spinal implant 310 is then advanced forward (distally), separating the arm members 214, 216 and distracting the disc space until the implant is located within the disc space. If necessary, the surgeon may attach an auxiliary instrument such as a T-Handle with an impaction plate onto the inserter 300 at the connector 309. The surgeon may then use a mallet to impact the implant 310 in between the arm members 214, 216 and into the disc space. Once the spinal implant 310 is in the proper location, the T-Handle is removed from the inserter 300 and handle assembly 216 is disengaged from the arm members 214, 216. To disengage the handle assembly 216, the locking knob 250 is returned to the unlocked position (e.g. rotated counterclockwise). The clamp arms 254 out of the clamp frame 274, the clamp arms 254 are able to flex outward such that the tapered lips 258 of the clamp arms 254 are able to pass over the outer surfaces 240 of the first and second arm members 214, 216 allowing removal of the first and second arm members 214, 216 from the receiving area 256. The first and second arm members 214, 216 are then removed individually by attaching a slap hammer (or other suitable instrument) to the connectors 242 on the first and second arm members 214, 216 and applying a force in a proximal direction. The surgeon then rotates the implant 310 to restore the desired height between the discs. The implant inserter 300 is then disengaged from the implant 310 and removed from the surgical access corridor. The surgical wound is then closed and the procedure is completed.

While specific embodiments have been shown by way of example in the drawings and described herein in detail, it will be appreciated that the invention is susceptible to various modifications and alternative forms. For example, although described primarily for use with a spinal fusion implant, the implant installation system 10 may be utilized to deliver other implants as well, such as for example, partial or total disc replacement implants, and corpectomy devices, among others. The description herein of specific embodiments is not intended to limit the invention to the particular forms disclosed, but on the contrary, the invention is to cover all modifications, equivalents, and alternatives falling within the spirit and scope of the invention.

We claim:

1. A medical implant guide assembly, comprising:
a first arm member including a generally planar first guide member having a proximal end, a distal end, a length dimension and a width dimension, the length dimension being greater than the width dimension, the proximal end including an attachment region having a first mating surface, a first semi-cylindrical recess extending longitudinally through the attachment region, and a first convex engagement surface extending semi-circumferentially around the attachment region, the distal end including a first distraction tang and a first abutment;
a second arm member including a generally planar second guide member having a proximal end, a distal end, a length dimension and a width dimension, the length dimension being greater than the width dimension, the proximal end including an attachment region having a second mating surface, a second semi-cylindrical recess extending longitudinally through the attachment region, and a second convex engagement surface extending semi-circumferentially around the attachment region, the distal end including a second distraction tang and a second abutment; and
a handle assembly lockingly attachable to the first and second arm members, the handle assembly including an inner member and an outer member, the inner member including a pair of clamp arms positioned at a first end of the inner member, a locking knob positioned at a second end of the inner member, and an elongated shaft extending between the clamp arms and locking knob, the clamp arms forming a generally U-shaped receiving area therebetween configured for engagement about the convex engagement surfaces of the first and second arm members, the clamp arms each having a tapered lip positioned at a distal end of the clamp arms and within the receiving area, the outer member including a contoured handle grip and a clamp frame, the clamp frame dimensioned to receive the clamp arms of the inner member therein, the locking knob being rotationally operable to move the handle assembly from a first, unlocked position permitting receipt of the engagement surfaces of the first and second arm members within the U-shaped receiving area, to a second, locked position which inhibits removal of the engagement surfaces of the first and second arm members from the U-shaped receiving area.

2. The guide assembly of claim 1, wherein the first guide member includes a first elongated side rail extending generally perpendicularly from one edge and along the length dimension of the first guide member, and the second guide member includes a second elongated side rail extending generally perpendicularly from one edge and along the length dimension of the second guide member.

3. The guide assembly of claim 2, wherein the first side rail has a first height dimension near the proximal end of the first guide member and a second height dimension near the distal end of the first guide member, the first height dimension being greater than the second height dimension.

4. The guide assembly of claim 2, wherein the second side rail has a first height dimension near the proximal end of the second guide member and a second height dimension near the distal end of the second guide member, the first height dimension being greater than the second height dimension.

5. The guide assembly of claim 1, wherein the first and second arm members mate at the first and second mating surfaces.

6. The guide assembly of claim 5, wherein the first and second semi-cylindrical recesses cooperate to form a cylindrical channel dimensioned to receive at least a portion of an insertion tool therethough.

7. The guide assembly of claim 5, wherein the first and second convex engagement surfaces cooperate to form a generally cylindrical engagement surface extending circumferentially around the outside of the first and second arm members.

8. The guide assembly of claim 7, wherein the generally cylindrical engagement surface is dimensioned to be received with the receiving area.

9. The guide assembly of claim 8, wherein the clamp arms are flexible to allow passage of the generally cylindrical engagement surface beyond the tapered lips and into the receiving area.

10. The guide assembly of claim 9, wherein the clamp frame is rigid.

11. The guide assembly of claim 10, wherein the clamp arms extend distally beyond the clamp frame while the handle assembly is in the first, unlocked position.

12. The guide assembly of claim 11, wherein rotatably operating the locking knob in a clockwise direction causes the clamp arms to be translated proximally into the clamp frame.

13. The guide assembly of claim 1, wherein the tapered lips each include a bi-directional taper.

14. A system for inserting a spinal implant within a target disc space, comprising:
  a spinal implant having a length dimension, a width dimension, a height dimension, a leading end, a trailing end, and first and second opposing vertebral engagement surfaces;
  an implant inserter an elongated shaft and an implant engagement feature at a distal end of the elongated shaft, the implant engagement feature configured to releasably engage the trailing end of the spinal implant; and
  a guide assembly having a first arm member mated with a second arm member and a handle assembly releasably coupled to the to the first and second arm members, the first and second arm members each including an elongated guide member having a proximal end and a distal end, the proximal end including an attachment region having a semi-cylindrical recess extending longitudinally therethrough such that the mated first and second arm members have a cylindrical channel extending therethrough, the first and second arm members each including a convex engagement surface extending semi-circumferentially around the attachment region such that the mated first and second arm members have a cylindrical engagement surface extending around the circumference of the mated first and second arm members, the handle assembly including an inner member and an outer member, the inner member including a pair of clamp arms positioned at a first end of the inner member, a locking knob positioned at a second end of the inner member, and an elongated shaft extending between the clamp arms and locking knob, the clamp arms forming a generally U-shaped receiving area therebetween configured for engagement about the convex engagement surfaces of the first and second arm members, the clamp arms each having a tapered lip positioned at a distal end of the clamp arms and within the receiving area, the outer member including a contoured handle grip and a clamp frame, the clamp frame dimensioned to receive the clamp arms of the inner member therein, the locking knob being rotationally operable to move the handle assembly from a first, unlocked position permitting receipt of the engagement surfaces of the first and second arm members within the U-shaped receiving area, to a second, locked position which inhibits removal of the engagement surfaces of the first and second arm members from the U-shaped receiving area.

\* \* \* \* \*